United States Patent [19]
Weidner et al.

[11] Patent Number: 6,051,729
[45] Date of Patent: Apr. 18, 2000

[54] PROCESS FOR PREPARING ORGANOSILAZANES

[75] Inventors: Richard Weidner, Burghausen; Walter Benischke, Mehring; Günther Uhlendorf, Burghausen, all of Germany

[73] Assignee: Wacker-Chemie GmbH, Munich, Germany

[21] Appl. No.: 09/177,941

[22] Filed: Oct. 23, 1998

[30] Foreign Application Priority Data

Dec. 2, 1997 [DE] Germany .............. 197 53 480

[51] Int. Cl.$^7$ ...................................... G07F 7/10
[52] U.S. Cl. .................. 556/412; 524/730; 528/10; 556/410
[58] Field of Search ............... 556/412, 410; 528/10; 524/730

[56] References Cited

U.S. PATENT DOCUMENTS 4,644,076  2/1987  Foster et al. .

FOREIGN PATENT DOCUMENTS

| | | |
|---|---|---|
| 26 45 703 | 6/1977 | Germany . |
| 26 45 703 B2 | 6/1977 | Germany . |
| 26 45 792 | 6/1977 | Germany . |
| 26 45 792 C2 | 6/1977 | Germany . |
| 1 516 899 | 7/1978 | United Kingdom . |
| 2 014 171 | 8/1979 | United Kingdom . |

OTHER PUBLICATIONS

Derwent Abstract (#77–27201Y/16) corresponding to DE 26 45 703.

Derwent Abstract (#77–27201Y/16) corresponding to DE 26 45 792.

*Primary Examiner*—Robert Dawson
*Assistant Examiner*—Jeffrey B. Robertson
*Attorney, Agent, or Firm*—Brooks & Kushmna P.C.

[57] ABSTRACT

A process for preparing organosilazane and ammonium chloride, by reaction of an organochlorosilane with ammonia in the presence of organosilazane as solvent, wherein ammonium chloride is removed from the resulting organosilazane and ammonium chloride-containing mixture, the improvement comprising adding an antiblocking agent to the mixture before removal, or to the ammonium chloride after its removal, such that a non-blocking, reusable ammonium chloride product is obtained.

6 Claims, No Drawings

PROCESS FOR PREPARING ORGANOSILAZANES

TECHNOLOGICAL FIELD

The invention relates to a process for preparing organosilazane and ammonium chloride.

DESCRIPTION OF THE RELATED ART

DE 26 45 703 B2 describes a process for preparing hexamethyldisilazane by reacting trimethylchlorosilane with gaseous ammonia in the presence of hexamethyldisilazane as solvent. The ammonium chloride formed in the reaction is removed from the hexamethyldisilazane by washing with water. The hexamethyldisilazane is then dried with sodium sulfate, and the sodium sulfate is filtered off. The disadvantages of this procedure for salt removal are that partial hydrolysis of the hexamethyldisilazane takes place on washing with water, and thus yield losses occur; the silazane requires subsequent treatment and filtration; and the ammonium chloride is produced in a non-reusable form as an aqueous solution.

In DE 26 45 792 C2, ammonium chloride is removed from hexamethyldisilazane by distillation under reduced pressure at a bottoms temperature below 75° C. These distillation conditions avoid sublimation of substantial quantities of ammonium chloride during the distillation of the hexamethyldisilazane, which otherwise would block the conduits. The ammonium chloride remaining in the reactor after the distillation, which still contains hexamethyldisilazane residues, is dissolved by adding dilute hydrochloric acid. The hexamethyldisilazane in the residue is thus converted to hexamethyldisiloxane and is removed as the lighter phase from the aqueous ammonium chloride. This process of salt removal has the disadvantage that the hexamethyldisilazane must be removed from the ammonium chloride by distillation, and thus very expensively. In addition, it is immediately evident to the skilled worker that this mode of removal can scarcely be implemented on the industrial scale since solid ammonium chloride, which is no longer stirrable, builds up as a residue in the reactor. This residue still contains hexamethyldisilazane, and thus loss in hexamethyldisilazane yield is unavoidable. Finally, ammonium chloride is once again obtained in non-reusable form as an aqueous solution.

Another possibility for salt removal consists of removing the ammonium chloride from the reaction mixture by filtration or centrifugal removal. The ammonium chloride, which still contains hexamethyldisilazane, is then dissolved in dilute hydrochloric acid, once again producing hexamethyldisiloxane and resulting in ammonium chloride as aqueous solution. Even with this procedure loss in yield of hexamethyldisilazane occurs, since considerable amounts of hexamethyldisilazane remain in the ammonium chloride on filtration or centrifugal removal.

Attempts to increase the yield of hexamethyldisilazane by subsequently removing the hexamethyldisilazane present in the ammonium chloride resulting from the filtration or centrifugal removal, for example by drying, fail on the industrial scale because, during the drying process with conventional drying equipment, the ammonium chloride sinters to relatively large, very hard agglomerates which are no longer amenable to technical manipulation and, moreover, make complete removal of the hexamethyldisilazane impossible.

All the existing processes have the disadvantage that loss in yield of hexamethyldisilazane occurs and the byproduct ammonium chloride is produced as an aqueous solution which is contaminated with organosilicon substances and consequently must be subjected to further purification, for example by biological processes, before release to the environment. Recovery of ammonium chloride is impossible or possible only with considerable and thus uneconomic expenditures.

Ammonium chloride is a valuable raw material inter alia for the fertilizer sector, for the explosives sector and for producing zinc/ammonium chloride melts. In addition, ammonium chloride is employed as nitrogen donor in municipal biological sewage treatment plants.

SUMMARY OF THE INVENTION

The object was to overcome the disadvantages of the prior art and, in particular, to provide a simple, economical environment-conscious process for preparing organosilazanes in which no losses of yield of the organosilazanes occur, and the ammonium chloride is obtained in solid, pure form which can be handled, i.e. is free-flowing and nonblocking, in order to make it available for the above-mentioned purposes of use.

DESCRIPTION OF THE PREFERRED EMBODIMENT

The invention relates to a process for preparing organosilazane and ammonium chloride, by reaction of an organochlorosilane with ammonia in the presence of organosilazane as solvent, wherein ammonium chloride is removed from the resulting mixture containing organosilazane and ammonium chloride by adding an antiblocking agent to the mixture before the removal, or to the ammonium chloride after the removal.

The organosilane is preferably trimethylchlorosilane, vinyldimethylchlorosilane, or mixtures thereof. The organosilazane used as solvent is preferably the same organosilazane it is intended to prepare. The process according to the invention is preferably used to prepare hexamethyldisilazane or 1,3-divinyltetramethyldisilazane. In the removal, the organosilazane is separated from the ammonium chloride.

Removal processes may be thermal processes or a combination of mechanical processes and thermal processes. A combination of mechanical processes and thermal processes is preferred. In a combination of mechanical and thermal processes, the mechanical process is carried out before the thermal process.

The mechanical process of removal preferably comprises filtration or centrifugal removal, with preference for centrifugal removal and, in particular, the use of a skimmer centrifuge.

If mechanical processes are used, the need for a residual content of organosilazane in the ammonium chloride for carrying out the granulation step described below means that these are carried out in such a way that the organosilazane content in the ammonium chloride after the mechanical removal is preferably in the range between 10 and 25% by weight.

Thermal processes for removal are preferably processes for drying which allow complete recovery of the organosilazane. Examples of devices suitable for drying are thin film dryers, fluidized bed dryers, spray dryers, band dryers and drum dryers, these dryers preferably being used when the antiblocking agent is added to the mixture before the removal, and the removal takes place by thermal processes. Further devices suitable for drying are dryers with which solid materials can be dried. These include, for example, plate dryers, rotary dryers, tumble dryers, double cone dryers and paddle dryers, with plate dryers being preferred. These dryers are preferably used when the removal takes place by a combination of mechanical and thermal processes. If the removal takes place by a combination of mechanical and thermal processes, it is possible, if the granulation step described below is not carried out and the antiblocking agent is added before the removal, for the removal also to take place with only a single device. Examples of devices of this type are heatable filter dryers, suction filter dryers and centrifuge dryers.

The drying is preferably carried out at a temperature from 50 to 150° C. under a pressure from 5 to 1000 hPa, particularly preferably at 65 to 130° C. under 10 to 500 hPa. The organosilazane content in the ammonium chloride after the drying is preferably below 500 ppm, particularly preferably below 350 ppm.

The antiblocking agent is added in amounts, based on ammonium chloride, of preferably 0.05 to 10% by weight, preferably in amounts of 0.05 to 3% by weight, particularly preferably in amounts of 0.1 to 2% by weight. It is possible to add only one type of antiblocking agent, but also various types of antiblocking agent and mixtures thereof.

The antiblocking agents used are preferably inorganic solid substances with average particle sizes of 0.01 to 50 $\mu$m. These include, for example, aluminum silicates, colloidal silica gel, pyrogenic silica, ground clays, perlites, vermiculites, gypsum, talc, cements, chalk powders, mixed calcium/magnesium carbonates or diatomaceous earth, with pyrogenic silica being preferred.

The reaction of organochlorosilane and ammonia in the presence of organosilazane as solvent can take place, for example, by the process described in DE 26 45 703 B2, which is incorporated herein by reference. In the preferred process, ammonia is passed into the mixture of organochlorosilane and organosilazane until no more is absorbed.

In the process according to the invention, the ammonium chloride content in the reaction mixture after the reaction of organochlorosilane and ammonia is preferably 10 to 40% by weight, particularly preferably 15 to 28% by weight. The ammonium chloride content can be adjusted in a simple manner through varying the content of organosilazane in the reaction.

An antiblocking agent described above can be added to this reaction mixture, and the removal can then be carried out by one of the processes described above, or the removal can be carried out first and then an antiblocking agent as described above can be added to the ammonium chloride.

If the antiblocking agent is added before the removal of the ammonium chloride, the removal preferably takes place thermally by one of the processes described above, or it can also take place mechanically by one of the processes described above in combination with a thermal process, in which case the mechanical removal preferably precedes the thermal removal. Removal by a combination of mechanical and thermal processes is preferred.

If the removal takes place by the combination of mechanical and thermal processes, a granulation step can then be carried out after the mechanical removal. The granulation of the ammonium chloride containing organosilazane or organosilazane and antiblocking agent is carried out using conventional wet granulation devices. The maximum dimensions of the resulting granule particles are in this case determined by the size of the holes in the granulation cylinder or other device used. Holes with sizes of from 1 to 10 mm are preferably employed, particularly preferably from 2 to 8 mm.

If the antiblocking agent is added after the removal, the ammonium chloride is removed by a combination of mechanical and thermal processes, in which case a granulation step as described above is necessary after the mechanical removal and before the thermal removal.

The dried ammonium chloride is preferably ground, the grinding preferably being to an average particle size (weight average) of from 10 to 600 $\mu$m, particularly preferably from 20 to 200 $\mu$m.

It is possible to use for the grinding all known grinding devices which can be used for such purposes. These include, for example, pinned disk mills, centrifugal flow mills, vibrating mills, pneumatic mills, drum mills, cone mills, toothed disk mills, roll mills, ball mills and pendulum mills.

The process according to the invention has the advantage that it is easy to carry out on the production scale, affords a high yield of organosilazane and is environmentally conscious because the resulting ammonium chloride can be reused.

Another advantage is that the resulting ammonium chloride has a high resistance to blocking and is very free-flowing, and thus no difficulties with handling, for example in emptying from containers, occur even after prolonged storage.

As a consequence of the low organosilazane content still present, the ammonium chloride prepared by the process according to the invention represents a non-hazardous material according to current regulations and can thus be reused universally in a more straightforward manner.

The ammonium chloride prepared by the process according to the invention has a purity, in terms of the content of environmentally relevant impurities such as, for example, the heavy metals lead, cadmium, chromium, nickel, zinc, copper and mercury, which is comparable with that of conventional ammonium chloride marketed in the specialist chemicals trade.

A preferred process A according to the invention for preparing organosilazanes, in particular hexamethyldisilazane and 1,3-divinyltetramethyldisilazane, takes place by reacting organochlorosilane and ammonia in the presence of organosilazane as solvent, and removing most of the organosilazane from the ammonium chloride formed in a first stage, granulating the ammonium chloride still containing organosilazane in a 2nd stage, removing and preferably recovering the organosilazane still present in the granules in a 3rd stage, and in a 4th stage, adding an antiblocking agent.

Grinding of the granules is carried out where appropriate before the 4th or after the 4th stage.

Another process B according to the invention for preparing organosilazanes, in particular hexamethyldisilazane and 1,3-divinyltetramethyldisilazane, takes place by reacting organochlorosilane and ammonia in the presence of organosilazane as solvent, and adding antiblocking agent to the reaction mixture containing ammonium chloride in a 1st stage, removing most of the organosilazane from the ammonium chloride in a 2nd stage, where appropriate, granulating the ammonium chloride still containing organosilazane in a 3rd stage, removing and preferably recovering the organosilazane still present in a 4th stage, grinding the resulting ammonium chloride where appropriate in a 5th stage, and adding further antiblocking agent, where appropriate, in a 6th stage.

The removal of the organosilazane from the ammonium chloride in the 2nd stage of process B and in the 1st stage of process A preferably takes place by the mechanical processes described above.

In the case where the 3rd stage is not carried out in process B, it is possible to combine the 2nd stage and the 4th stage together in such a way that the removal of the ammonium chloride and the removal therefrom of the remaining organosilazane take place using a single device. Examples of devices suitable for this purpose are filter dryers, suction filter dryers and centrifuge dryers.

In the following examples, all data in parts and percentages are based on weight unless otherwise indicated. Unless otherwise indicated, the following examples are carried out under the pressure of the surrounding atmosphere, that is to say about 1000 hPa, and at room temperature, that is to say about 20° C.

The ammonium chloride produced has been assessed for its resistance to blocking. To determine the resistance to blocking, the material to be investigated was packed into an iron pipe (height: 100 mm; diameter: 50 mm) with screw thread, then loaded with a metal plunger weighing 3 kg (diameter: 49 mm) and subsequently stored in a drying oven at 50° C. for 16 hours. After cooling to room temperature, the metal plunger was cautiously removed, the screw closure was opened and the material was removed from the pipe. If the material was extensively blocked, it was cautiously pushed out of the iron pipe using the metal plunger. The resistance to blocking was determined qualitatively by crushing the material and was assessed using the following scoring scheme:

1=Free-flowing and pourable

2=Powder flows with assistance out of the iron pipe, with some lumps. Some lumps remain and disintegrate on shaking.

3=Cylinder of powder which has been pushed out partly disintegrates. Remaining lumps disintegrate to floury material under gentle pressure.

4=Cylinder of powder which has been pushed out can be broken up very easily. Resulting lumps can very easily be crushed to a powder almost without residue.

5=Cylinder of powder which has been pushed out can be broken up very easily. Very few lumps which can very easily be broken up are produced.

6=Cylinder of powder which has been pushed out can be broken up easily. Many small and relatively large lumps which can easily be broken up are produced.

7=Cylinder of powder which has been pushed out can be broken up easily. Many small and relatively large lumps which can be broken up are produced.

8=Powder cylinder which has been pushed out can be broken up only by very heavy pressure. Many small and relatively large hard lumps remain.

9=Cylinder of powder which has been pushed out cannot be broken up by pressure. It remains a coarse, hard and lumpy material.

1–3=No risk of blocking

4–5=Scarcely any risk of blocking

6–7=Critical range

8–9=Material blocks

The organosilazane content in the ammonium chloride was determined by $^1$H-NMR. The average particle size was determined using an LS particle size analyzer (Coulter LS 130).

COMPARATIVE EXAMPLE 1

950 parts by weight of trimethylchlorosilane and 1161 parts by weight of hexamethyldisilazane were placed in a reaction vessel. Gaseous ammonia was passed into this mixture. The reaction was started at 20° C., and the temperature rose to 45° C. while ammonia was being passed in. The reaction mixture was then kept at this temperature by cooling the reaction vessel. After passing in ammonia for 90 minutes, absorption of ammonia had ceased. Nevertheless, the ammonia supply was continued at a reaction temperature 45° C. for a further 45 minutes. The reaction mixture was then cooled to room temperature. The reaction with ammonia had produced a mixture of 80% by weight hexamethyldisilazane and 20% by weight ammonium chloride (dispersion A).

The hexamethyldisilazane was removed from this mixture by centrifugation using a skimmer centrifuge. The resulting ammonium chloride (ammonium chloride A) had a hexamethyldisilazane content of 15.8% by weight after the centrifugal removal.

300 g of the ammonium chloride A were then dried in a rotary evaporator at a temperature of 110° C. under a vacuum of 50 hPa for 2 hours. During the drying, the ammonium chloride agglomerated to very hard particles of stable shape and various sizes.

After powdering, the dried ammonium chloride had an average residual hexamethyldisilazane content of 3000 ppm and a blocking resistance of 8.

Drying attempts starting from dispersion A and ammonium chloride A were carried out on the industrial scale using the following dryer systems at 110° C. and 50 hPa:

Vacuum plate dryer (VTT system) from Krauss Maffei, Munich, Germany (ammonium chloride A)

Vacuum filter dryer from Rosemund, Liesthal, Switzerland (dispersion A)

Suction filter dryer from Seitz Filterwerke, Bad Kreuznach, Germany (dispersion A)

Vertical/horizontal thin film dryer from Künzi, Bubendorf, Switzerland (dispersion A)

Titus centrifuge dryer from Fima, Obersontheim, Germany (dispersion A)

With all types of dryer, the ammonium chloride caked after a short time to hard particles of cherry to snowball size, and in the case of the thin film dryer hard deposits, which gradually became glassy, formed between the rotor and the walls, so that the drying process had to be stopped in all cases.

After powdering, the resulting ammonium chloride had a blocking resistance of 8.

COMPARATIVE EXAMPLE 2

Ammonium chloride A was granulated using a granulator from Alexanderwerke (Remscheid, Germany) with holes 3–5 mm in size. The resulting ammonium chloride granules had a stable shape. Using the vacuum plate dryer from Krauss Maffei used in Comparative Example 1, the granules were then dried without technical difficulties at 110° C. and 50 hPa to recover the hexamethyldisilazane present in ammonium chloride A. There was no caking of the granules during the drying.

After powdering, the resulting ammonium chloride had a hexamethyldisilazane content of 250 ppm and a blocking resistance of 8.

EXAMPLE 1

The dried ammonium chloride obtained in Comparative Example 2 was ground with a double pinned disk mill (Alpine Labor Condux) at 34,000 revolutions per minute to an average particle size of 66 μm (weight average) and then mixed with 0.5% pyrogenic silica with the name Wacker HDK® H 30 (from Wacker-Chemie GmbH, Munich, Germany) with a BET surface area of 250 m$^2$/g and a carbon content of 1.9%.

The silica-containing ammonium chloride showed a blocking resistance of 2.

EXAMPLE 2

1%, based on the ammonium chloride present in dispersion A, of pyrogenic silica with the name Wacker HDK® N 20 (from Wacker-Chemie GmbH, Munich, Germany) with a BET surface area of 200 m$^2$g was mixed into dispersion A. The hexamethyldisilazane was then removed by centrifugation using a skimmer centrifuge. The resulting silica-containing ammonium chloride (ammonium chloride B) had a hexamethyl-disilazane content of 16.5% by weight after the centrifugal removal.

300 g of ammonium chloride B were then dried in a rotary evaporator at a temperature of 110° C. under a vacuum of 50 hPa for 2 hours. The ammonium chloride did not form lumps during the drying. The resulting product was a powder which had an average residual hexamethyldisilazane content of 120 ppm, a blocking resistance of 2 and an average particle size of 309 μm (weight average).

EXAMPLE 3

Ammonium chloride B was dried on the industrial scale, using the vacuum plate dryer from Krauss Maffei used in Comparative Example 1, without technical difficulties at 110° C. and 50 hPa to recover the hexamethyldisilazane present in ammonium chloride B. The ammonium chloride did not cake during the drying.

The resulting product was a powder with an average residual hexamethyldisilazane content of 140 ppm, a blocking resistance of 2 and an average particle size of 280 μm (weight average).

EXAMPLE 4

0.5%, based on the ammonium chloride present in dispersion A, of the pyrogenic silica used in Example 1 was mixed in. The hexamethyldisilazane was then removed by centrifugation using a skimmer centrifuge. The resulting silica-containing ammonium chloride (ammonium chloride C) had a hexamethyldisilazane content of 14.3% by weight after the centrifugal removal.

Ammonium chloride C was granulated in analogy to Comparative Example 2. Despite the silica addition, ammonium chloride granules of stable shape were obtained. The granules were then dried using the vacuum plate dryer from Krauss Maffei used in Comparative Example 1 at 110° C. and 50 hPa to recover the hexamethyldisilazane present. The granules did not cake during the drying but partly disintegrated into smaller particles. The dried granules were then ground in analogy to Example 1 to an average particle size of 64 μm (weight average).

Determination of the residual hexamethyldisilazane content showed a value of 210 ppm, and determination of the blocking resistance showed a value of 3. After further addition of 0.5% of the pyrogenic silica used in Example 1, the resulting powder was free-flowing with a blocking resistance of 1.

EXAMPLE 5

The silica-containing dried ammonium chloride from Example 1 was investigated by AES (atomic emission spectroscopy) for its content of lead, cadmium, chromium, nickel, zinc, copper and mercury. The content of all these elements was below 5 ppm.

What is claimed is:

1. In a process for preparing organosilazane and ammonium chloride by reaction of an organochlorosilane with ammonia in the presence of organosilazane as solvent, wherein ammonium chloride is removed from the resulting organosilazane and ammonium chloride-containing reaction mixture, the improvement comprising
   a) adding an antiblocking agent to the reaction mixture before the removal of ammonium chloride,
   b) adding an antiblocking agent to the ammonium chloride after its removal from the reaction mixture, or
   c) adding an antiblocking agent to the reaction mixture before removal of ammonium chloride and also to the ammonium chloride after its removal from the reaction mixture.

2. A process for preparing organosilazane and ammonium chloride as claimed in claim 1, wherein said antiblocking agent is added before the removal of ammonium chloride from the reaction mixture, and the removal of the ammonium chloride takes place thermally or by a combination of mechanical and thermal processes.

3. A process for preparing organosilazane and ammonium chloride as claimed in claim 2, wherein the removal takes place by a combination of mechanical and thermal processes, and a granulation step is carried out after the mechanical removal.

4. A process for preparing organosilazane and ammonium chloride as claimed in claim 2 wherein additionally antiblocking agent is added to the ammonium chloride after the removal.

5. A process for preparing organosilazane and ammonium chloride as claimed in claim 3 wherein additionally antiblocking agent is added to the ammonium chloride after the removal.

6. A process for preparing organosilazane and ammonium chloride as claimed in claim 1, wherein the antiblocking agent is added to the ammonium chloride after its removal from the reaction mixture, the removal of the ammonium chloride takes place by a combination of mechanical and thermal processes, and a granulation step is carried out after the mechanical removal and before the thermal removal.

* * * * *